(12) United States Patent
Cottrell

(10) Patent No.: US 6,218,589 B1
(45) Date of Patent: Apr. 17, 2001

(54) METHOD FOR IMPROVING THE OPERATION OF A PROPANE-PROPYLENE SPLITTER

(75) Inventor: Paul R. Cottrell, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/483,332

(22) Filed: Jan. 14, 2000

Related U.S. Application Data

(63) Continuation-in-part of application No. 09/268,057, filed on Mar. 15, 1999, now abandoned, which is a continuation-in-part of application No. 08/855,126, filed on May 13, 1997, now abandoned.

(51) Int. Cl.[7] .............................. C07C 7/167; C07C 5/333
(52) U.S. Cl. ..................... 585/324; 585/654; 585/655; 585/314; 585/315; 585/258; 585/259
(58) Field of Search ..................................... 585/654, 655, 585/314, 315, 324, 258, 259

(56) References Cited

U.S. PATENT DOCUMENTS

| | | | |
|---|---|---|---|
| 4,430,517 | 2/1984 | Imai et al. | 585/444 |
| 4,438,288 | 3/1984 | Imai et al. | 585/379 |
| 4,523,045 | 6/1985 | Vora | 585/254 |
| 4,761,509 | 8/1988 | Vora et al. | 585/254 |

*Primary Examiner*—Walter D. Griffin
*Assistant Examiner*—Thuan D. Dang
(74) *Attorney, Agent, or Firm*—John G. Tolomei; John F. Spears, Jr.; John G. Cutts, Jr.

(57) ABSTRACT

A method for improving the operation of a propane-propylene splitter in a process for the dehydrogenation of propane wherein the propane is dehydrogenated to produce a stream containing propylene and trace quantities of methyl acetylene and propadiene compounds and which stream is selectively hydrogenated to selectively saturate at least a majority of the trace quantities of methyl acetylene and propadiene compounds. The resulting effluent from the selective hydrogenation zone is fractionated in a propane-propylene splitter to produce a high-purity propylene product stream, an unconverted propane stream which is introduced to the dehydrogenation zone and a small slip stream or side-cut containing methyl acetylene and propadiene compounds which is introduced into the selective hydrogenation zone.

5 Claims, 1 Drawing Sheet

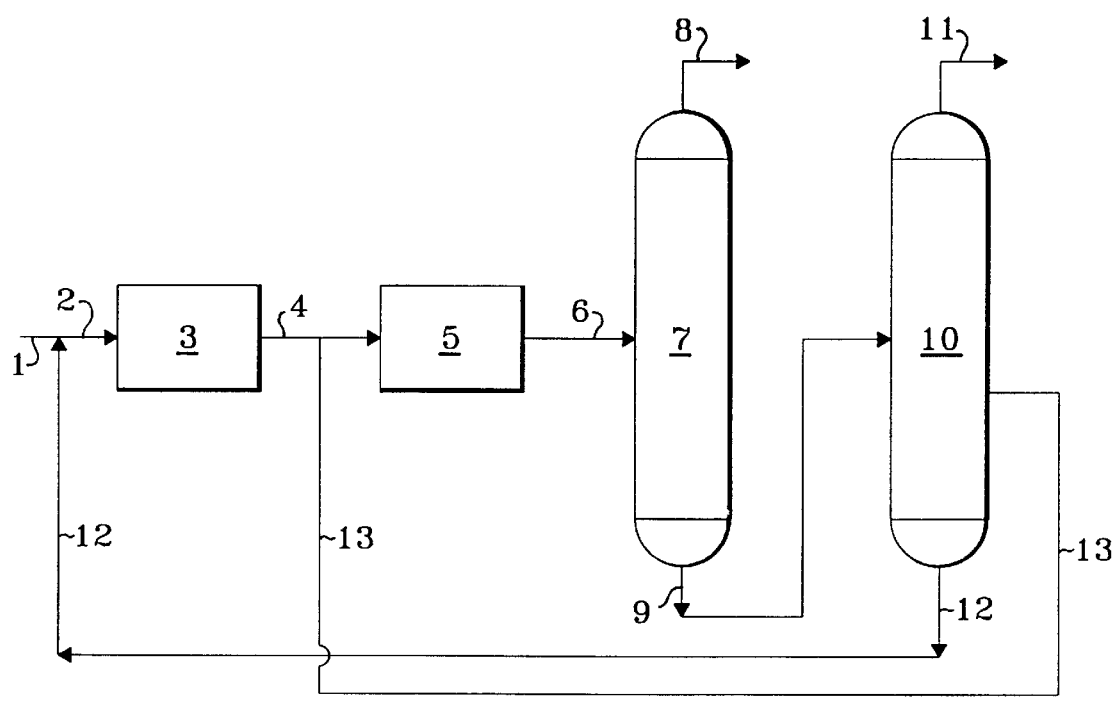

METHOD FOR IMPROVING THE OPERATION OF A PROPANE-PROPYLENE SPLITTER

CROSS REFERENCE TO RELATED APPLICATIONS

This application is a continuation-in-part of U.S. Application Ser. No. 09/268,057 filed Mar. 15, 1999 now abandoned, which is a continuation-in-part of U.S. Application Ser. No. 08/855,126 filed May 13, 1997 now abandoned, both of which are incorporated herein by reference.

BACKGROUND OF THE INVENTION

The field of art to which this invention pertains is the production of high purity propylene and a method for improving the operation of a propane-propylene splitter.

INFORMATION DISCLOSURE

Processes for the production of olefin hydrocarbons are very useful in the production of a great number of petrochemical products as well as motor fuel blending components. The short chain paraffins having from 2 to 5 carbon atoms per molecule are often subjected to dehydrogenation to form the corresponding olefin. The normal paraffin hydrocarbon having 2 to 5 carbon atoms per molecule is preferably selected from the group consisting of ethane, propane, butane and pentane. The olefins, in turn, are used, for example, in the alkylation of isoparaffins or in the etherification of alcohols to make motor fuel blending components.

U.S. Pat. No. 4,523,045 (Vora) discloses a process for the production of linear olefinic hydrocarbons wherein a feed stream comprising at least one $C_4$ to $C_{20}$ feed paraffinic hydrocarbon is dehydrogenated in a dehydrogenation zone and the resulting effluent is selectively hydrotreated in order to selectively hydrogenate diolefins and the resulting stream is stripped to remove light hydrocarbon gases and is introduced into an adsorptive separation zone to produce a stream comprising olefins and a stream containing paraffins and trace quantities of diolefins and other highly dehydrogenated hydrocarbon compounds. The resulting recovered paraffin stream from the adsorptive separation zone is then admixed with fresh feed and directly introduced into the paraffin dehydrogenation zone. The trace quantities of diolefins and methyl acetylene compounds are rapidly converted to coke in the dehydrogenation zone and this resulting coke is deposited on the charge heater tubes and dehydrogenation catalyst which shortens the life of the catalyst. This patent fails to disclose the recovery of a stream containing an enriched concentration of methyl acetylene and propadiene from a propane-propylene splitter column and the subsequent introduction of this stream into a selective diolefin hydrogenation zone to convert these impurities into propylene.

U.S. Pat. No. 4,761,509 (Vora et al) discloses a process for the catalytic dehydrogenation of paraffinic hydrocarbons.

U.S. Pat. No. 4,430,517 (Imai et al) discloses a catalyst for the conversion of hydrocarbons. The catalyst comprises a platinum group component, a Group IVA component, an alkali or alkaline earth component and a porous carrier material wherein the atomic ratio of the alkali or alkaline earth component to the platinum group component is more than 10. This catalyst is particularly useful for dehydrogenating paraffins having from 2 to 5 or more carbon atoms to the corresponding mono-olefins.

U.S. Pat. No. 4,438,288 (Imai et al) discloses a process for dehydrogenating hydrocarbons which comprises contacting a dehydrogenatable hydrocarbon in a dehydrogenation zone with a catalyst comprising a platinum group component, an alkali or alkaline earth component and a porous support material to produce a dehydrogenated hydrocarbon and a used catalyst; contacting the used catalyst in a catalyst regeneration zone with a halogen component to produce a regenerated catalyst containing added halogen component; and contacting a dehydrogenatable hydrocarbon in a dehydrogenation zone with the resulting regenerated catalyst to produce a dehydrogenated hydrocarbon and a used catalyst.

Currently, propane is dehydrogenated to produce propylene and hydrogen with the concomitant production of low levels of methyl acetylene and propadiene. The resulting effluent from a propane catalytic dehydrogenation reaction zone is subsequently fractionated to produce a high purity propylene product stream and a high purity stream of unconverted propane. The nature of the equilibrium of the propane and propylene with the methyl acetylene and propadiene allows the methyl acetylene and propadiene to concentrate in an identifiable central portion of the fractionator. This fractionator is frequently referred to as the propane-propylene splitter.

In the event of an upset in the fractionator, the high concentration of methyl acetylene and propadiene can impact either the marketability of the propylene product because of impurity contamination or cause severe coking if these impurities are recycled together with propane to the dehydrogenation catalyst.

In order to alleviate the buildup of highly unsaturated impurities such as methyl acetylene and propadiene, the dehydrogenation reactor effluent has been selectively hydrogenated to reduce the levels of these highly unsaturated impurities before any subsequent fractionation. Although the hydrogenation is relatively selective towards the highly unsaturated compounds, the very nature of the hydrogenation catalyst is to saturate compounds with hydrogen and if the olefin is hydrogenated there will necessarily be a loss of the desired olefin product. Therefore, the operating conditions of the selective hydrogenation zone are adjusted to balance the hydrogenation of the undesired highly unsaturated compounds including methyl acetylene and propadiene with the maximization of the olefin product.

In accordance with the present invention, it has been unexpectedly discovered that even the reduced levels of highly unsaturated compounds remaining after the selective hydrogenation can accumulate to undesirable levels in the product fractionator and still cause problems with the maximum production of high quality propylene. With the present invention, the accumulation of the highly unsaturated compounds is identified and removed from the fractionation zone and introduced into the selective hydrogenation zone to thereby permit the maximum production of high purity propylene product and to prevent excessive, premature coking of the dehydrogenation catalyst.

BRIEF SUMMARY OF THE INVENTION

It has now been found that an improved propane dehydrogenation process can be achieved by removing and recovering a small side-cut stream from the propylene product fractionator and introducing this side-cut stream containing methyl acetylene and propadiene compounds to a selective hydrogenation reaction zone. When the present invention is utilized, the high quality of the propylene product is ensured if not enhanced and any possible premature coking of the dehydrogenation catalyst is also ensured.

The invention provides a process for the dehydrogenation of propane by means of contacting the propane and hydrogen with a dehydrogenation catalyst to produce a stream containing propylene, hydrogen and trace quantities of methyl acetylene and propadiene. This resulting stream is selectively hydrogenated to hydrogenate at least a majority of the highly unsaturated impurities, i.e., methyl acetylene and propadiene without any significant hydrogenation of the desired propylene. The resulting selectively hydrotreated stream is then fractionated in a propane-propylene splitter to produce a high purity product stream containing propylene, a propane hydrocarbon stream which is recycled to the dehydrogenation zone and a small slip stream containing highly unsaturated impurities including methyl acetylene and propadiene which is introduced into the selective hydrogenation zone.

One embodiment of the present invention is a method for improving the operation of a propane-propylene splitter which method comprises the steps of: (a) contacting propane and hydrogen with a dehydrogenation catalyst at dehydrogenation conditions in a dehydrogenation zone to produce a first stream comprising propylene, propane, hydrogen and trace quantities of methyl acetylene and propadiene; (b) contacting at least a portion of the first stream comprising propylene, propane, hydrogen and trace quantities of methyl acetylene and propadiene with a selective hydrogenation catalyst at selective hydrogenation conditions in a selective hydrogenation zone to selectively saturate at least about 90% of the trace quantities of methyl acetylene and propadiene; (c) fractionating at least a portion of the resulting effluent from the selective hydrogenation zone in a propane-propylene splitter to produce a second stream comprising high purity propylene and a third stream comprising high purity propane; (d) identifying and removing a fourth stream in an amount of about 0.1 to about 2 weight percent of the propane feed to the dehydrogenation zone comprising propylene, propane and trace quantities of methyl acetylene and propadiene in an amount of about 100 wppm to about 20,000 wppm from the propane-propylene splitter; (e) introducing the fourth stream produced in step (d) into the selective hydrogenation zone in step (b) to selectively saturate the methyl acetylene and propadiene; and (f) recovering the second stream comprising high purity propylene.

BRIEF DESCRIPTION OF THE DRAWING

The drawing is a simplified process flow diagram of a preferred embodiment of the present invention.

DETAILED DESCRIPTION OF THE INVENTION

Fresh propane feed is combined with recycle hydrogen and recycled unconverted propane to form a reactant stream which is passed through a bed of suitable dehydrogenation catalyst in a catalytic propane dehydrogenation zone maintained at the proper dehydrogenation conditions to produce a stream comprising propylene, propane, hydrogen and trace quantities of methyl acetylene and propadiene and this effluent stream from the catalytic propane dehydrogenation reaction zone is passed to a selective hydrogenation zone.

The effluent from the catalytic propane dehydrogenation zone contains propylene, propane, hydrogen and trace quantities of methyl acetylene and propadiene. Since these highly unsaturated impurities, i.e., methyl acetylene and propadiene are detrimental to the final product propylene stream and the longevity of the dehydrogenation catalyst, it is necessary to selectively hydrogenate the highly unsaturated impurities to propylene. The selective hydrogenation zone is preferably operated at selective hydrogenation conditions which minimize the hydrogenation of propylene and maximize the saturation of the highly unsaturated compounds, i.e., methyl acetylene and propadiene. This balancing of operating conditions will produce an effluent stream which will contain reduced trace quantities of the highly unsaturated compounds. This resulting effluent is then fractionated in a fractionation zone and more particularly a propane-propylene splitter to produce an overhead stream containing propylene and a bottoms stream containing unconverted propane which is recycled to the dehydrogenation zone to produce additional propylene. A central draw stream containing highly unsaturated compounds, i.e., methyl acetylene and propadiene is identified, isolated and removed from the fractionation zone (propane-propylene splitter) and introduced into the selective hydrogenation zone.

In accordance with the present invention, the effluent from the propane dehydrogenation zone is selectively hydrogenated to selectively saturate at least about 90% of the trace quantities of methyl acetylene and propadiene. During the fractionation in the propane-propylene splitter, a stream in an amount of about 0.1 to about 2 weight percent of the propane feed to the dehydrogenation zone containing propylene, propane and trace quantities of methyl acetylene and propadiene in an amount of about 100 wppm to about 20,000 wppm is isolated and removed from the propane-propylene splitter, and introduced into the selective hydrogenation zone to selectively saturate the methyl acetylene and propadiene compounds.

The composition of the dehydrogenation catalyst is not believed to materially affect the operation of the subject process provided this catalyst meets commercial standards for activity, stability and selectivity. Dehydrogenation catalysts are described in U.S. Pat. Nos. 3,274,287; 3,315,007; 3,315,008; 3,745,112; and 4,430,517. These catalysts comprise a platinum group component supported on a porous carrier material. The preferred carrier material is a refractory inorganic oxide such as gamma-alumina. The preferred dehydrogenation catalysts contain on an elemental basis 0.01 to 2 wt. % platinum group component and about 0.1 to 5 wt. % of an alkali or alkaline earth metal. Preferably, there is present 0.05 to 1 wt. % platinum group component and about 0.25 to 3.5 wt. % of the alkali or alkaline earth component. The platinum group component may be chosen from the group consisting of platinum, palladium, rhodium, ruthenium, osmium and iridium, but platinum is highly preferred. The alkali or alkaline earth component may be selected from the group consisting of the alkali metals--cesium, rubidium, potassium, sodium and lithium; and the alkaline earth metals--calcium, strontium, barium and magnesium. This component is preferably either lithium or potassium. Another example of a suitable dehydrogenation catalyst is a catalyst which, in addition to the previously described platinum and alkali or alkaline earth metal components, contains a tin component. This catalytic composite would contain from 0.1 to about 1 wt. % tin. Yet another catalytic composite which should be highly suited for use in the subject process comprises an indium component in addition to the platinum, tin and alkali or alkaline earth components. The indium component may be present on an elemental basis equal to about 0.1 to about 1 wt. % of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt. %. A halogen component is not desired in all situations. These catalytic composites are known to those skilled in the art and are described in the available references.

In accordance with the present invention, dehydrogenation conditions include a pressure from about 0 psig to about 100 psig (689 kPa gauge) and a temperature from about 752° F. (400° C.) to about 1292° F. (700° C.).

The composition of the selective hydrogenation catalyst is not believed to materially affect the operation of the present invention provided that this catalyst meets commercial standards for activity, stability and selectivity. Suitable selective hydrogenation catalysts include at least one noble metal selected from Group VIII which includes ruthenium, rhodium, palladium, osmium, iridium and/or platinum on a carrier material. Another suitable selective hydrogenation catalyst contains nickel. Palladium is the preferred metal. Any one of the usual carrier materials may be used, for example, alumina, silica-alumina, carbon and the like, with a preferred carrier material being alumina. The preferred catalyst comprises a composition and contains from about 0.01 to about 2 percent by weight of palladium on an alumina carrier material.

The feed to the selective hydrogenation zone including the stream from the fractionation zone (propane-propylene splitter) is contacted with the selective hydrogenation catalyst in the presence of hydrogen at selective hydrogenation conditions including a pressure from about 100 psig (689 kPa gauge) to about 800 psig (5516 kPa gauge) and a temperature in the range from about 85° F. (29° C.) to about 575° F. (302° C.). The highly unsaturated compounds, i.e., methyl acetylene and propadiene, are saturated to a level greater than about 90%.

The resulting effluent from the selective hydrogenation zone is introduced into a fractionation zone referred to as a propane-propylene splitter to produce a high purity overhead stream comprising propylene and a bottoms stream comprising propane. A small slip stream containing methyl acetylene and propadiene compounds is isolated and removed as a side-cut from the splitter and introduced into the selective hydrogenation zone. The side-cut stream is preferably in an amount from about 0.01 weight percent to about 2 weight percent of the fresh feed propane to the dehydrogenation zone. In general, the operating conditions of the propane-propylene splitter are known and the appropriate draw point of the side-cut stream containing methyl acetylene and propadiene will be readily determined by a person skilled in the art.

DETAILED DESCRIPTION OF THE DRAWING

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the techniques involved. The use of such miscellaneous equipment is well within the purview of one skilled in the art.

With reference now to the drawing, a fresh propane feed stream is introduced into the process via line 1 and is admixed with a recycle propane stream provided via line 12 and the resulting admixture is introduced via line 2 into dehydrogenation zone 3. The resulting effluent from dehydrogenation zone 3 containing propylene, propane and trace quantities of highly unsaturated compounds, i.e., methyl acetylene and propadiene, is removed via line 4 and admixed with a stream containing methyl acetylene and propadiene provided via line 13 and the resulting admixture is introduced into selective hydrogenation zone 5. The resulting effluent from hydrogenation zone 5 containing a reduced concentration of highly unsaturated compounds is transported via line 6 and introduced into deethanizer 7. A light gaseous stream containing $C_{2-}$ compounds is removed from deethanizer zone 7 via line 8. A $C_{3+}$ stream is removed from deethanizer 7 via line 9 and introduced into propane-propylene splitter 10. A resulting high purity propylene product stream is removed from propane-propylene splitter 10 via line 11 and recovered. An unconverted propane stream is removed from propane-propylene splitter 10 via line 12 and is recycled to dehydrogenation zone 3 as described hereinabove. A dragstream (side-cut stream) is removed from an intermediate zone of propane-propylene splitter 10 via line 13 and is introduced into selective hydrogenation zone 5 as described hereinabove.

The process of the present invention is further demonstrated by the following illustrative embodiment. This illustrative embodiment is, however, not presented to unduly limit the process of this invention, but to further illustrate the advantages of the hereinabove-described embodiment. The following results were not obtained by the actual performance of the present invention but are considered prospective and reasonably illustrative of the expected performance of the invention based upon sound engineering calculations.

ILLUSTRATIVE EMBODIMENT

A fresh feed stream in an amount of 100 mass units of propane and a recycle stream of 150 mass units per hour of propane is introduced into a catalytic propane dehydrogenation zone containing a dehydrogenation catalyst containing platinum and alumina operated at a pressure of about 30 psig and a temperature of about 1200° F. to produce a stream containing 100 mass units per hour of propylene, 200 ppm of propadiene and methyl acetylene, and the balance propane. This resulting effluent stream is introduced into a selective hydrogenation zone containing a selective hydrogenation catalyst containing palladium operated at a pressure of about 500 psig and a temperature of about 160° F. to saturate about 90 percent of the propadiene and methyl acetylene with a retention of the propylene of about 99.5 percent. The resulting effluent from the selective hydrogenation zone is introduced into a fractionation zone including a propane-propylene splitter to produce an overhead stream containing 100 mass units per hour of propylene and a bottoms stream containing 149 mass units per hour of propane which is recycled to the catalytic dehydrogenation zone. A slip stream (side-cut) is withdrawn from an intermediate point in the propane-propylene splitter in an amount of 1 mass unit per hour and containing 2000 wppm of propadiene and methyl acetylene and introduced into the selective hydrogenation zone in order to saturate the propadiene and methyl acetylene. In the event that the slip stream from the splitter to the selective hydrogenation zone is discontinued, the concentration of propadiene and methyl acetylene in the central portion of the propane-propylene splitter increases to an undesirable level of about 18,000 wppm.

The foregoing description, drawing and illustrative embodiment clearly illustrate the advantages encompassed by the process of the present invention and the benefits to be afforded with the use thereof.

What is claimed:

1. A method for improving the operation of a propane-propylene splitter which method comprises the steps of:

(a) contacting propane and hydrogen with a dehydrogenation catalyst at dehydrogenation conditions in a dehydrogenation zone to produce a first stream comprising propylene, propane, hydrogen and trace quantities of methyl acetylene and propadiene;

(b) contacting at least a portion of said first stream comprising propylene, propane, hydrogen and trace quantities of methyl acetylene and propadiene with a selective hydrogenation catalyst at selective hydrogenation conditions in a selective hydrogenation zone to selectively saturate at least 90% of said trace quantities of methyl acetylene and propadiene;

(c) fractionating at least a portion of the resulting effluent from said selective hydrogenation zone in a propane-propylene splitter to produce a second stream comprising high purity propylene and a third stream comprising high purity propane;

(d) identifying and removing a fourth stream in an amount of about 0.1 to about 2 weight percent of the propane fed to the dehydrogenation zone comprising propylene, propane and trace quantities of methyl acetylene and propadiene in an amount of about 100 wppm to about 20,000 wppm from said propane-propylene splitter;

(e) introducing said fourth stream produced in step (d) into said selective hydrogenation zone in step (b) to selectively saturate said methyl acetylene and propadiene; and (f) recovering said second stream comprising high purity propylene.

2. The process of claim 1 wherein said dehydrogenation conditions include a pressure from about 0 psig to about 100 psig (689 kPa gauge) and a temperature from about 752° F. (400° C.) to about 1292° F. (700° C.).

3. The process of claim 1 wherein said dehydrogenation catalyst comprises platinum.

4. The process of claim 1 wherein said selective hydrogenation catalyst comprises palladium.

5. The process of claim 1 wherein said selective hydrogenation conditions include a pressure from about 100 psig (689 kPa gauge) to about 800 psig (5516 kPa gauge) and a temperature from about 85° F. (29° C.) to about 575° F. (302° C.).

\* \* \* \* \*